United States Patent
Warkentine et al.

(10) Patent No.: US 8,382,766 B2
(45) Date of Patent: Feb. 26, 2013

(54) CONNECTION OF CUTTING BLOCKS

(75) Inventors: Blaine Warkentine, Royersford, PA (US); Norman Plaβky, Erfurt (DE); Manuel Millahn, München (DE)

(73) Assignee: Brainlab AG, Feldkirchen (DE)

( * ) Notice: Subject to any disclaimer, the term of this patent is extended or adjusted under 35 U.S.C. 154(b) by 582 days.

(21) Appl. No.: 12/468,080

(22) Filed: May 19, 2009

(65) Prior Publication Data

US 2009/0287216 A1  Nov. 19, 2009

Related U.S. Application Data

(60) Provisional application No. 61/056,610, filed on May 28, 2008.

(30) Foreign Application Priority Data

May 19, 2008 (EP) ...................................... 08156468

(51) Int. Cl.
- *A61B 17/58* (2006.01)
- *A61B 17/60* (2006.01)
- *A61F 2/00* (2006.01)

(52) U.S. Cl. .......................................... 606/88; 606/87

(58) Field of Classification Search ................ 606/86 R, 606/87, 88, 75, 105, 151; 600/238; 403/286, 403/300; D6/325; D8/364, 381
See application file for complete search history.

(56) References Cited

U.S. PATENT DOCUMENTS

| | | | |
|---|---|---|---|
| 4,524,766 A | 6/1985 | Petersen | |
| 4,566,448 A | 1/1986 | Rohr, Jr. | |
| 5,520,695 A | 5/1996 | Luckman | |
| 5,524,999 A * | 6/1996 | Morbitzer | 403/27 |
| 5,735,904 A * | 4/1998 | Pappas | 606/86 R |
| 6,648,541 B1 * | 11/2003 | Zimmer et al. | 403/286 |
| 6,796,986 B2 * | 9/2004 | Duffner | 606/87 |
| 7,318,827 B2 * | 1/2008 | Leitner et al. | 606/87 |
| 2006/0167460 A1 | 7/2006 | Pinczewski et al. | |
| 2006/0235290 A1 * | 10/2006 | Gabriel et al. | 600/407 |
| 2007/0118138 A1 | 5/2007 | Seo et al. | |

FOREIGN PATENT DOCUMENTS

FR    2 840 797    12/2003

* cited by examiner

*Primary Examiner* — Andrew Yang
(74) *Attorney, Agent, or Firm* — Renner, Otto, Boisselle & Sklar, LLP (57) ABSTRACT

The present application relates to a surgical connecting device for connecting a first and second cutting block which each serve to make an incision on a first and second anatomical structure, comprising: a first attaching section for attaching the surgical connecting device to the first cutting block by a mechanical connection; a second attaching section for attaching the surgical connecting device to the second cutting block by a releasable mechanical connection; and a spacing section which spaces the first attaching section away from the second attaching section.

17 Claims, 11 Drawing Sheets

CONNECTION OF CUTTING BLOCKS

RELATED APPLICATION DATA

This application claims the priority of U.S. Provisional Application No. 61/056,610, filed on May 28, 2008, which is hereby incorporated in its entirety by reference.

FIELD OF THE INVENTION

The present application relates to the connection of cutting blocks. Cutting blocks are used in surgery, in particular for cutting body structures (bones, in particular the femur and tibia).

BACKGROUND OF THE INVENTION

Preferably, the invention is used in image-assisted navigation (image-guided surgery or IGS). Attaching marker devices to a body structure—for example, a reference star to a bone—and attaching a marker device to a cutting block allows a cutting block to be navigated relative to the body structure and thus allows the cutting block to be positioned exactly relative to the body structure, at a planned location. In order to position the cutting block exactly, an adjusting mechanism is used which is likewise fixed to the bone. In accordance with the prior art, one adjusting mechanism for each cutting block is fixed to the body structure.

SUMMARY OF THE INVENTION

It is an object of the invention, when using two or more cutting blocks, to enable the number of fixing processes for fixing the adjusting mechanisms to the body structure and/or the number of adjusting mechanisms used to be reduced.

In accordance with the invention, damage to the body structure is advantageously avoided to a greater extent than in the prior art, since fewer fixations are performed. The space requirement is advantageously less, since fewer adjusting mechanisms—in particular, only one adjusting mechanism—is needed. The invention can advantageously reduce the operation time and thus reduce the burden on the patient.

The aforesaid object is solved by the subjects of the independent claims. Advantageous developments follow from the dependent claims.

Preferably, the invention relates to a surgical connecting device for connecting a first and second cutting block. Preferably, the surgical connecting device is used in the region of a joint, wherein a first incision on a first body part (for example, the tibia) is to be made by the first cutting block, and an incision on a second body part (for example, the femur) is to be made by the second cutting block. The first and second body part are connected by the joint. The incision is in particular made in order to crop an end of the first and second body part which faces the joint, i.e. which is in particular situated in the vicinity of the joint. The cutting blocks serve to guide a cutting knife and to define a plane in which the incision is to be made using the cutting knife. The cutting blocks in particular comprise two cutting guidance planes which are preferably parallel to each other and between which the blade of a cutting knife can be guided. The distance between the cutting guidance planes corresponds at least approximately to the thickness of the blade or is slightly larger. The cutting guidance planes thus determine the position of the cutting plane in which the incision is made by means of the blade.

The surgical connecting device in accordance with the invention preferably comprises a first and second attaching section. The first attaching section is formed so as to be able to attach the surgical connecting device to the first cutting block. The second attaching section is formed so as to be able to attach the surgical connecting device to the second cutting block. The first and second attaching sections are preferably formed so as to form a mechanical connection between the surgical connecting device and the respective cutting block. The mechanical connection is preferably releasable and preferably ensures a spatially fixed connection. Examples of a mechanical connection are a positive-fit connection, a force-fit connection or a material-fit connection. Preferably, a positive-fit connection and/or force-fit connection is achieved with the aid of the attaching section. To this end, special contact sections can also be provided on the cutting blocks, via which the attaching sections establish a releasable mechanical connection, in particular a releasable force-fit connection and/or positive-fit connection, when they contact the contact sections, in order to attach the surgical connecting device. The connection can for example be an exact fit and/or a locking connection. Apart from special contact sections on the cutting blocks, the attaching sections can also be formed such that they can be introduced into the gap between the cutting guidance planes of the cutting block, in order to establish a force-fit connection and/or positive-fit connection with the cutting guidance planes.

The surgical connecting device also preferably comprises a spacing section which spaces the first attaching section away from the second attaching section. This results in a defined and fixed positional relationship between the first and second cutting blocks, when both cutting blocks are connected to the surgical connecting device. Preferably, the distance is selected such that the surgical connecting device can be gripped by a surgeon, in particular even with gloves. The spacing section is in particular configured such that the positional relationship (in particular the distance) between the first and second cutting block can be (mechanically) adjusted, such that the surgical connecting device can be adapted to the respective body structure by the surgeon. To this end, it is also possible to select from different surgical connecting devices having different fixed distances (for example, 18 mm, 19 mm and 20 mm) between the first and second attaching section. In particular, the lower limit for the extent of the spacing is around 1 mm, preferably around 1 cm. The upper limit for the spacing is preferably around 20 cm, more preferably around 10 cm, even more preferably around 5 cm or 3 cm. A typical distance between the first and second attaching section is for example around about 19 mm.

If the spacing section is configured such that the distance can be adjusted by means of an adjusting mechanism, then the spacing section preferably comprises two parts which are movable relative to each other, the relative position of which can be mechanically determined by a fastening means (for example a setting screw which passes through slits in the movable parts) or a locking connection. In this way, the distance between the attaching sections can then be altered, at least to a predetermined extent, to the desired distance. The locking mechanism and/or the aforementioned fastening means, for example in conjunction with the slits, form examples of an adjusting mechanism using which the distance between the first and second attaching section can be adjusted.

The spacing section is in particular preferably formed to be large enough to be able to attach a handle to it.

An intermediate space in which space is provided for the cutting guidance planes of the cutting blocks and/or for contact sections of the cutting blocks is preferably provided between the first and second attaching section. The intermediate space between the first and second attaching section is therefore preferably not completely filled. In particular, the first attaching section is preferably not connected to the second attaching section over the shortest distance by the spacing section. Preferably, the spacing section runs at least partially and preferably at least predominantly outside the intermediate space between the first attaching section and the second attaching section. The intermediate space between the first and second attaching section is in particular the space given by directly and linearly connecting the boundaries of the first attaching section to the boundaries of the second attaching section.

The boundaries of the attaching sections comprise boundary sections, such as a front end and a rear end of the attaching sections. The front end is characterized in that it precedes during the process of attaching the connecting section to the cutting block, i.e. it has the shortest distance from the cutting block as compared to the other parts of the surgical connecting device, wherein this distance is reduced further and further as the surgical connecting device is moved nearer and nearer to the cutting block, in order to connect the surgical connecting device to the cutting block. The rear end is situated opposite the front end. The rear end is characterized in that it is connected to the spacing section. The front end of the attaching section is in particular formed as an edge of the surgical connecting device, which in particular forms an end of a planar section of the attaching device. This arrangement of the spacing section relative to the attaching sections enables a defined spacing of the cutting blocks. It also prevents parts of the cutting block from obstructing or blocking the connecting device from being attached to the cutting blocks.

In accordance with another embodiment of the present invention, the attaching sections comprise movable parts and contact parts. The contact parts are preferably spatially fixed relative to the spacing section. The movable parts are preferably movable, in particular elastically movable, relative to the contact parts and in particular also relative to the spacing section. The movable parts can for example comprise elastic elements such as springs or rubber. However, they can also be elastically connected to a part of the attaching section, in particular to the contact parts. The movable parts can for example be elements (for example, metallic or plastic elements) which are only connected in sections, in particular only one section, to other parts of the attaching section, in particular to the contact parts. This connection in sections can in particular be formed to be elastic. In particular, the movable parts can be bent out of a plane relative to the other parts, in particular relative to the contact parts. If a force is exerted on the movable parts, in order to move them towards the contact parts, then an elastic force counteracts this due to the elastic formation of the movable parts. The movable parts are in particular elastically movable relative to a plane which virtually or actually connects the front end and the rear end of the attaching sections and/or in which the contact parts lie. In particular, the movement is performed out of the plane, i.e. in particular transverse to the plane. The contact parts are preferably formed to be planar and preferably lie in the aforesaid plane, or the surfaces of the contact parts define the aforesaid plane. In particular, the contact parts do not comprise any extensions protruding transverse to the plane. Forming the contact parts to be planar allows them to be inserted into the contact sections of the cutting blocks and in particular between the cutting guidance planes. They can in particular be formed such that they can be inserted in an exact fit.

The movable parts are preferably formed such that the edges of the movable parts which protrude out of the aforesaid plane between the front end and the rear end draw nearer and nearer to said plane in the direction of the front end of the attaching sections, i.e. they are preferably chamfered in the direction of the front end. This has the advantage that as the attaching sections are introduced, the movable parts are pressed ever-increasingly in the direction of the plane, if the attaching section is inserted into a gap—for example, cutting guidance surfaces—or into a groove-shaped contact section.

Preferably, the surgical connecting device comprises abutment sections which serve to exactly position the surgical connecting device relative to the cutting blocks. To this end, the abutment sections preferably protrude out of the aforesaid plane between the front end and rear end, such that when the attaching section is inserted into a gap, the gap boundaries abut the abutment sections. The gap is for example formed between the cutting guidance planes or by the contact section of the cutting block. Preferably, an abutment section is provided between the spacing section and each of the connecting sections.

Preferably, the surgical connecting device comprises a marker device. The exact position of the surgical connecting device can be detected by means of the marker device. Since the relative position of the surgical connecting device relative to the cutting blocks is known, in particular due to the cutting blocks abutting the abutment sections, the position of the cutting blocks can also be determined by detecting the marker device which is attached to the surgical connecting device.

Preferably, other surgical instruments or surgical devices can be attached to the surgical connecting device. In particular, a patella cutting apparatus can be attached to the surgical connecting device, in order to be able to crop the patella. The patella is situated between the femur and the tibia. Since the surgical connecting device is situated between the two cutting blocks, which serve to cut the tibia and femur, respectively, it is situated at a suitable location for cutting the patella. If the surgical connecting device in accordance with the invention comprises the patella cutting apparatus or a way of attaching a patella cutting apparatus, then this automatically results in a suitable position of the patella cutting apparatus during the operation.

The invention is also directed to a surgical system which comprises both the surgical connecting device and two cutting blocks which are formed for being connected to the surgical connecting device. Preferably, the system also comprises an adjusting mechanism which can be or is connected to a cutting block. The adjusting mechanism is preferably attached to a bone, for example the tibia. Adjusting operational parts are preferably attached to the adjusting mechanism, such as for example wheels, using which it is possible to change the position of the cutting block which is connected to the adjusting mechanism, relative to the part or parts of the adjusting mechanism which are fixedly connected to the bone. The advantages which this has in conjunction with the surgical connecting device in accordance with the invention are described in the following on the basis of a method in accordance with the invention.

As mentioned, the adjusting mechanism is preferably first fastened to a first body structure (for example, the tibia) using fastening means (for example, pins or nails). In a following step, the adjusting mechanism is connected to the first cutting block, or is already connected to the first cutting block when it is fastened to the first body structure. A marker device is preferably attached to a component of the system, such that changes in position caused by the adjusting mechanism can be detected by detecting the marker device. The marker device can for example be attached to the part of the adjusting mechanism which is or can be connected, spatially fixed, to the first cutting device and which changes its position relative to the first body structure by actuating the adjusting mechanism. It can be attached to the first cutting block or it can be attached to the surgical connecting device in accordance with the invention, if the latter is already connected to the first cutting block. If the second cutting block is also already connected to the surgical connecting device, then the marker device can also be attached to the second cutting block. In this state, a spatially fixed connection between the first and second cutting block is in particular provided by means of the connecting device.

It is then possible to determine the position of the second cutting block by detecting the marker device. This position can be changed by actuating adjusting means on the adjusting mechanism. The marker device is thus spatially fixed relative to the parts of the adjusting mechanism for which a change in position relative to the bone is possible. It is in particular not spatially fixed relative to the parts of the adjusting mechanism which are fixed (spatially fixed) relative to the first body structure. It is in particular spatially fixed relative to the part of the adjusting mechanism which is formed for and in particular establishes a spatially fixed connection to the first cutting block.

If the situation just described is given, then the position of the second cutting block is preferably adjusted relative to the second body part (for example, the femur), wherein the adjustment is monitored by means of the marker device and detecting the same. For example, the position of both the first body structure and the cutting block is displayed, by means of a navigation system, on a monitor of the navigation system. The navigation system in particular comprises a data processing device which processes the detection signals which are input into the data processing device from a camera. The camera detects said marker device.

Preferably, the initial state is one in which the connecting device connects the first and second cutting block. The marker device is also preferably attached, spatially fixed, relative to the first cutting block. Since a connection between the first and second cutting block is provided by the surgical connecting device, a spatially fixed connection of the marker device relative to the second cutting block is also given in the state specified. Alternatively or additionally, a separate marker device can also be attached to the second cutting block.

In the following, a first approach for fixing the two cutting blocks is described. A second, alternative approach is illustrated in conjunction with FIG. 7.

In a first step, the position of the second cutting block relative to the second body structure is then preferably adjusted by means of the adjusting mechanism, by means of a marker device which is connected, spatially fixed, to the second cutting block. Once the desired position has been reached, the second cutting block is fixed to the second body structure. Once it has been fixed, the surgical connecting device is removed, such that the second cutting block is movable relative to the first cutting block. In a second step, the first cutting block is then moved relative to the first body structure, into the desired position, by means of the adjusting mechanism. A marker device which is connected, spatially fixed, to the first cutting block is used for this. The first cutting block is then fixed to the first body structure. Thus, both the first and second cutting block are attached to the first and second body structure, respectively, and exactly positioned. In the position then given, the incision is made on the respective body structure with the aid of the fixed cutting blocks.

Optionally, the adjusting mechanism can be removed from the first body structure before the incision is made. Before the surgical connecting device is removed, a patella cutting device can also be attached to it. Alternatively, the surgical connecting device can already comprise the patella cutting device. The patella is then preferably cut before the surgical connecting device is removed.

The invention also relates to: a surgical system comprising the surgical connecting device in accordance with the invention; a navigation system comprising the surgical system; and the use of the surgical connecting device, the surgical system and/or the navigation system.

BRIEF DESCRIPTION OF THE DRAWINGS

Other advantages and features of the invention are disclosed in the following detailed description. Different features and different embodiments can be combined with each other.

DETAILED DESCRIPTION

Figure 1:
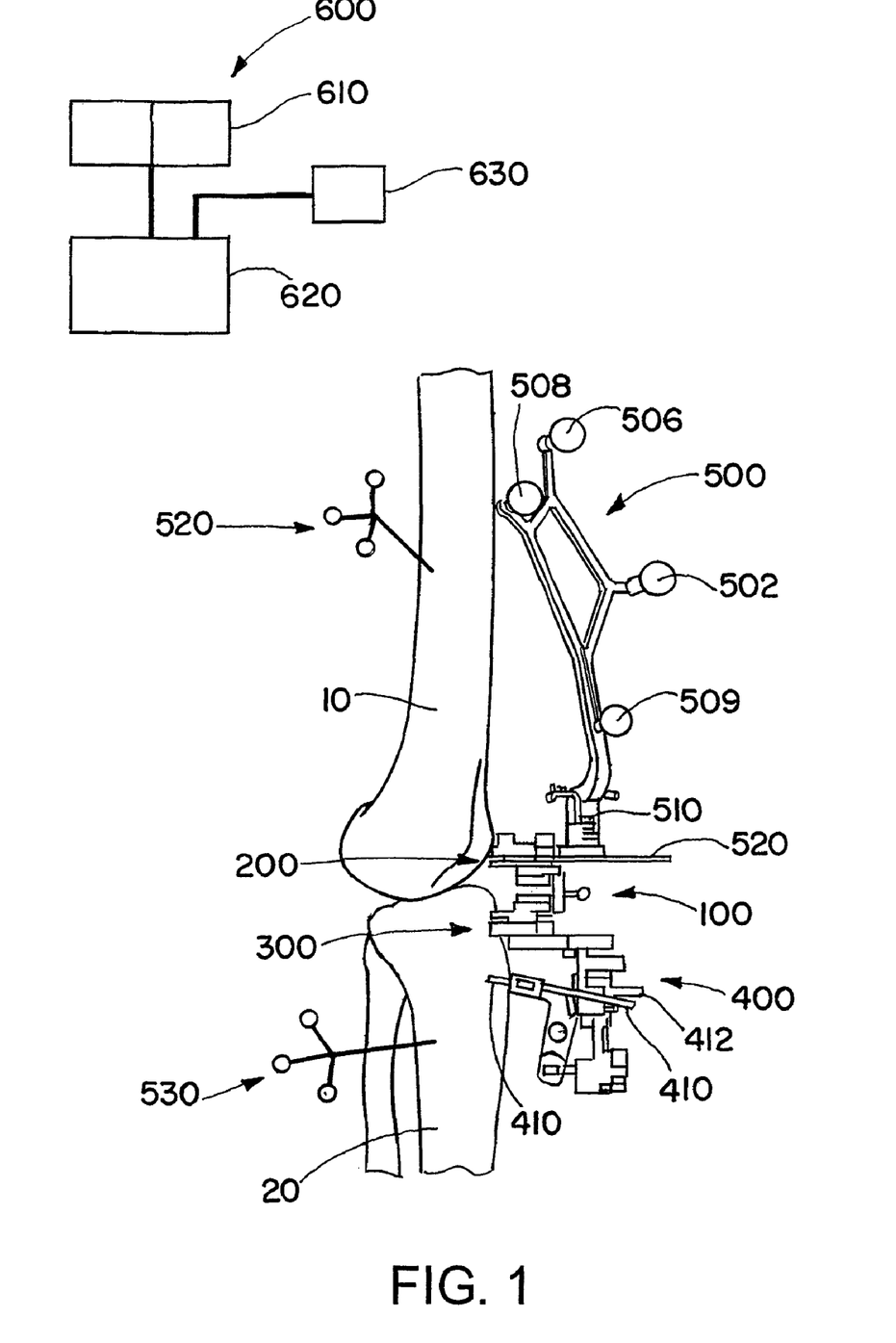
FIG. 1 shows a navigation system of the present invention, comprising a navigation device and a surgical system in accordance with the present invention.

FIG. 1 shows a surgical system in accordance with the present invention, comprising the components 100, 200, 300, 400 and 500, which are illustrated in more detail in the following. The system comprises the surgical connecting device 100 in accordance with the invention. FIG. 1 also shows a femur 10 and a tibia 20 and a navigation device 600. Preferably, only one adjusting mechanism 400 is provided in accordance with the invention and attached to the tibia 20 via pins 410 and 412. This one adjusting mechanism is sufficient, due to the use of the surgical connecting device 100 which connects a tibial cutting block 300 (the first cutting block) to a femoral cutting block 200 (the second cutting block) for adjusting the fixed position of the two cutting blocks. A reference star 500 is connected, spatially fixed, to the femoral cutting block 200. In the embodiment shown, the reference star 500 is releasably connected via a snap-on connection 510 to a platform 520 which is in turn connected to the second cutting block 200. The platform 520 can for example be inserted between the cutting guidance surfaces of the cutting block. In particular, it comprises abutment points in order to have a defined position of the reference star 500 relative to the cutting block 200, in particular relative to the cutting guidance planes, and/or a defined relative position of the cutting plane relative to the reference star. In order to determine the relative position as exactly as possible, abutment points or locking elements are preferably provided on the platform 520 and can be moved to abut or engage with the cutting block. The platform 520 can also be formed such that it can be inserted between the cutting guidance planes into the cutting block (200 or 300) in as exact a fit as possible. A defined relative position between the cutting guidance planes and the reference star is thus given. The relative position is known to and stored in the navigation device 600.

Figure 2:
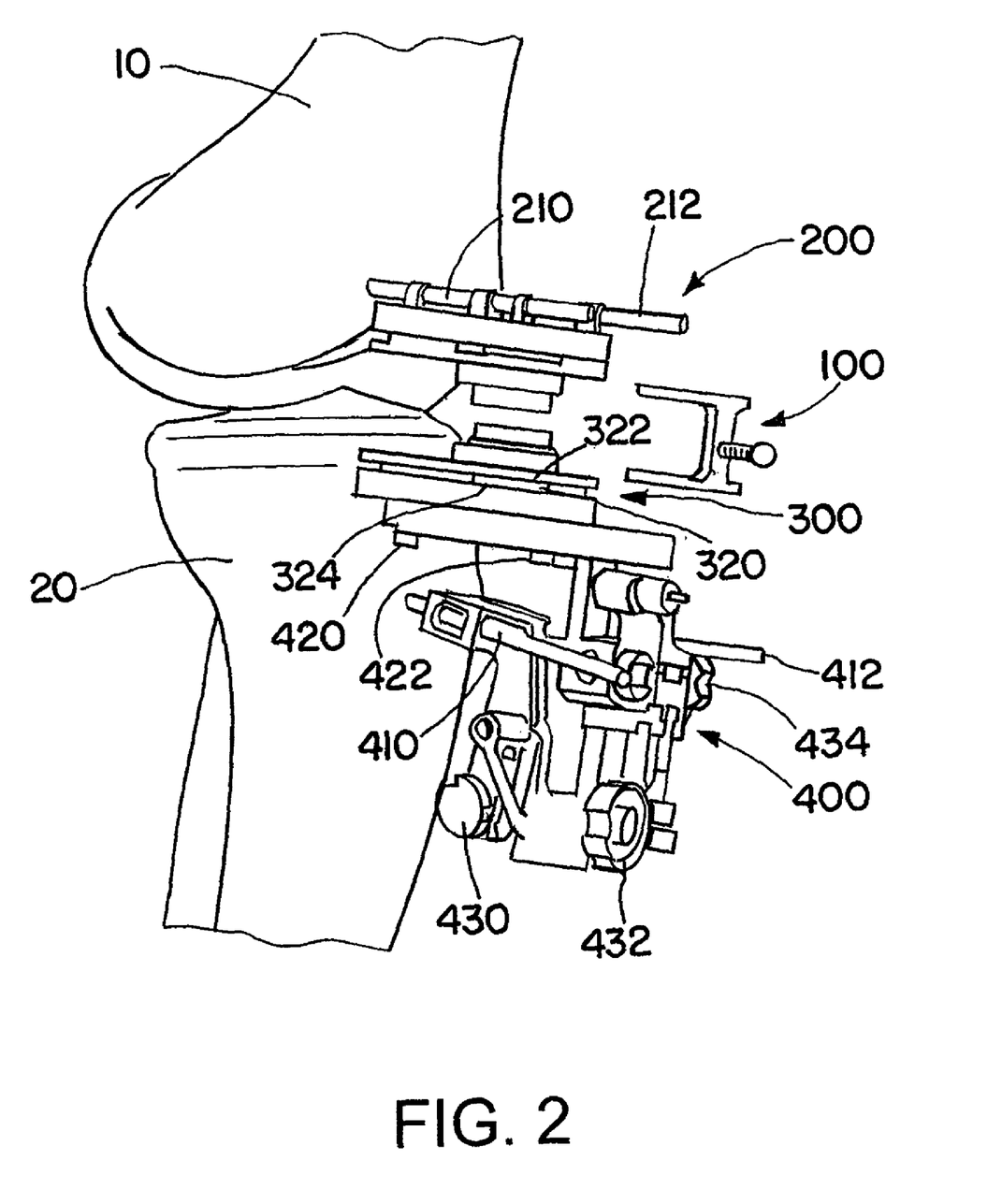
FIG. 2 shows a surgical system in accordance with the present invention, wherein the connecting device in accordance with the invention is just being removed.

The reference star 500 for example comprises marker elements 502, 504, 506 and 508 which can in particular be formed to be spherical. The marker elements can be formed to be active or passive. Active marker elements actively emit radiation or waves. Passive marker elements reflect radiation or waves. The radiation can in particular be electromagnetic radiation such as UV light, visible light or infrared light. The waves can in particular be ultrasound waves. The marker elements preferably have a pre-defined position relative to each other which is typical of the reference star 500, such that the reference star 500 can be identified by a navigation device 600. The navigation device 600 in particular comprises a detection device 610 consisting for example of two camera elements. It also preferably comprises a data processing device 620 which processes the detection signals of the detection device 610, in particular in order to ascertain position data of the reference star 500 from them. Due to the known relative position between the reference star 500 and the cutting plane, this allows the position of the cutting plane to be calculated in a reference frame which is used by the navigation device. Reference stars are preferably likewise provided in the relevant body parts, i.e. for example a reference star 520 in the femur 10 and a reference star 530 in the tibia. Preferably, the relative position of a three-dimensional model of the body part (the femur or tibia) relative to the reference star (520 or 530) fixed to the body part is known to and in particular stored in the navigation device. It is therefore possible to determine the position of the cutting plane relative to the respective body part, i.e. for example relative to the femur 10 or tibia 20, by means of the data processing device 620. The data processing device 620 can then display the calculated result, in particular the relative positional relationship between a model of the body part (the femur and/or tibia) and the cutting plane, on a monitor 630, and/or can transmit a signal to the monitor 630, upon which said relative positional relationship is displayed on the monitor 630. In this way, a surgeon can change the position of the cutting plane by adjusting the adjusting mechanism 400, and check the position of the cutting plane on the monitor 620. If the surgeon considers the position of the cutting plane relative to the femur 10, in particular as displayed on the monitor 630, to be a match or in accordance with the plan, the cutting block 200 can then be fastened to the femur 10 by means of pins (not visible in FIG. 1). FIG. 2 shows how this would then look after the reference star 500 and the surgical connecting device 100 have been removed. In FIG. 2, pins 210 and 212 are shown which are inserted into the femur 10 in order to fasten the cutting block 200 to the femur in the desired position. The connecting device 100 is just being removed.

Once the connecting device 100 has been removed, the position of the first cutting block 300 is preferably then adjusted. A reference star is preferably again used for this, for example the reference star 500 which is shown in FIG. 1. The reference star, which is preferably fastened to a platform (for example, the platform 520), is connected to the cutting device 300 such that a defined position (which is known to the navigation device 600) of the cutting plane of the cutting block 300 relative to the reference star 500 is obtained. To this end, said platform 520 can for example be inserted into the gap 320 between the cutting guidance planes 322 and 324. The platform is preferably formed to be an exact fit in the gap 320, such that this cannot result in any tilting of the platform relative to the cutting plane. Alternatively, other connecting options for connecting the reference star to one of the cutting blocks 200, 300 can of course also be used, as has also been stated above. Locking connections can in particular be provided on the cutting block 200, 300, in particular such that inserting the platform 520 into the gap 320 is not necessary, but rather a connection between the reference star 500 and the cutting block 200, 300 is established outside the gap 320.

The cutting block 300 is connected, preferably mechanically and preferably releasably, to the adjusting mechanism 400. In particular, fastening means 420 and 422 are preferably provided on the adjusting mechanism 400. By releasing these fastening means 420, 422 (for example, screws), it is then possible to remove the adjusting mechanism 400 from the cutting block 300, if this is desired. A plurality of adjusting screws 430, 432, 434, etc. are provided on the adjusting mechanism 400, in order to be able to change the position of the cutting block 300 relative to the pins 412 and 410 via which the adjusting mechanism 400 is fastened to the tibia 20. The position is also changed in this case until the desired position of the cutting block 300, i.e. the desired position of the cutting plane of the cutting block 300, relative to the tibia 20 has been achieved.

By way of the surgical connecting device 100, the adjusting mechanism 400 can accordingly be used twice. On the one hand, it can be used to adjust the position of the cutting block 200, and can then also be used to adjust the position of the cutting block 300. In this way, only one adjusting mechanism 400 has to be fastened to the bone, and damage to the bone is thus reduced.

Figure 3:
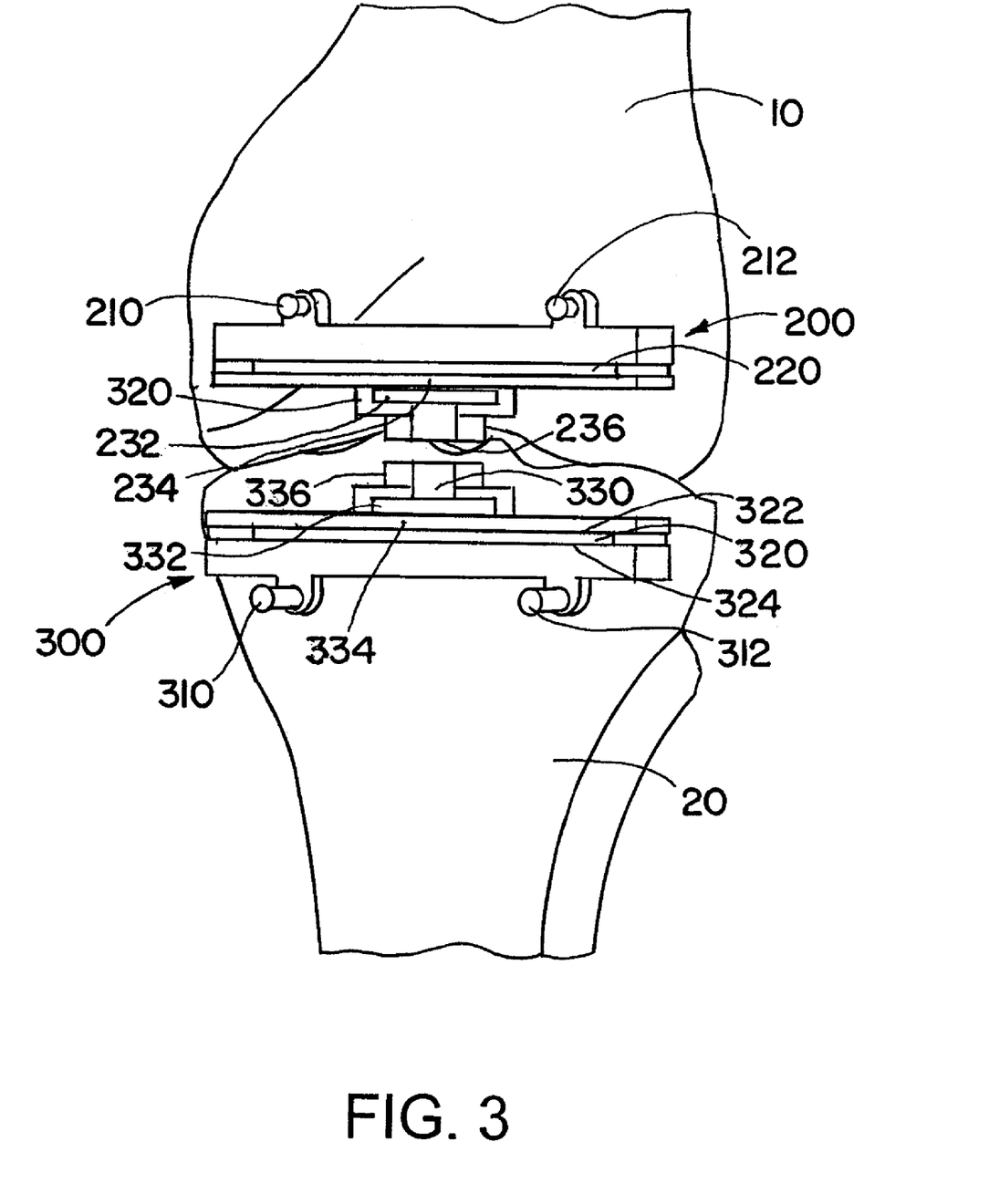
FIG. 3 shows two cutting blocks which are not connected and are fixed to the bone.

FIG. 3 shows the situation after the surgical connecting device 100, the adjusting mechanism 400 and the reference star 500 (not shown in FIG. 2) have been removed. Identical reference signs designate identical parts. This also applies to the other figures.

In the state shown in FIG. 3, the tibial cutting block 300 is fastened to the tibia 20 at the desired position by pins 310, 312.

Figure 4:
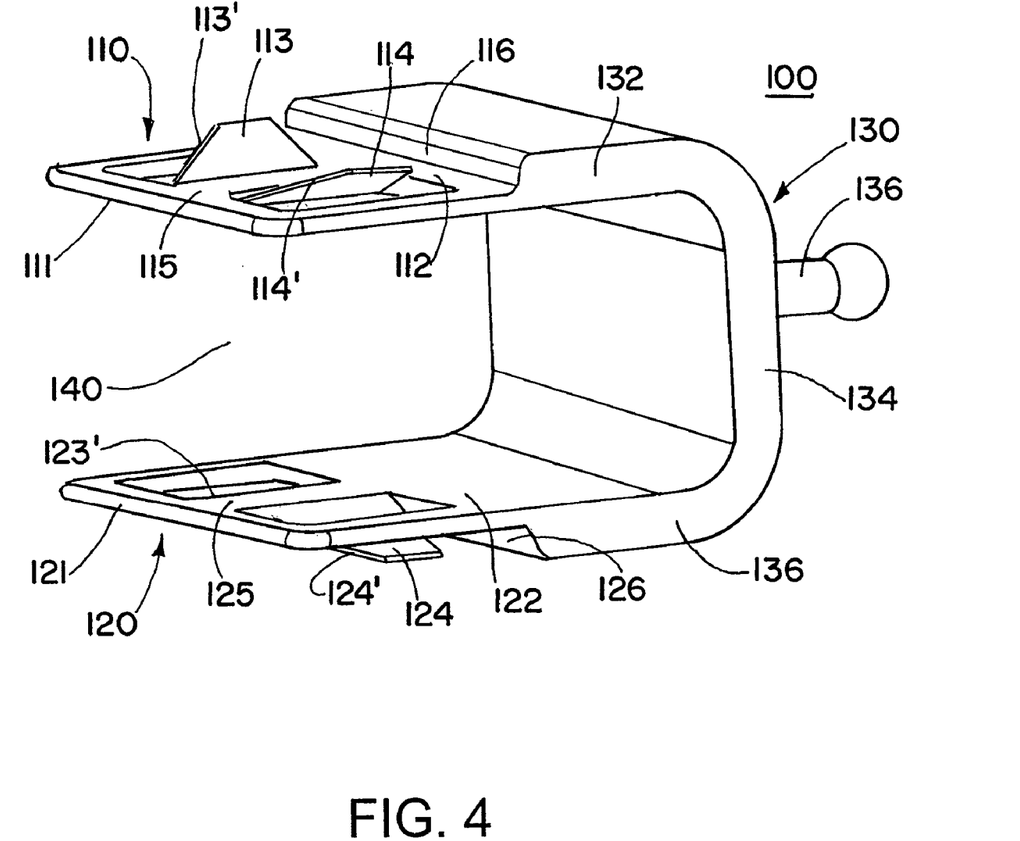
FIG. 4 shows an embodiment of the surgical connecting device in accordance with the invention.

FIG. 4 shows the structure of a surgical connecting device 100 in accordance with the invention. The surgical connecting device 100 comprises front ends 111 and 121 which can each be inserted into contact gaps 232 and 332 of contact sections 230 and 330. The thickness of the front ends and in particular of the contact parts 115 and 125 is preferably smaller than or equal to the gap thickness of the contact gaps 230 and/or 330. Preferably, the contact parts 115 and 125 are formed to be an exact fit with the contact gaps 230 and 330. The contact parts are preferably formed to be planar. In the section 112 of the contact part 115 facing away from the front end 111, the contact part is preferably connected to the spacing section 130, preferably integrally connected. The contact part 115 can however also be attached to the spacing section 130 in the region 112 using fastening means. In the embodiment shown, the contact part 115 is formed to be planar. Movable parts 113 and 114 are movable relative to the contact part 115. In the embodiment shown, these movable parts are molded onto the contact part 115, in particular integrally with it. Due to their material formation (for example, metal or plastic), the movable parts can be moved, in particular elastically, relative to the contact part by the action of a force. This means that after the action of the force ends, they automatically return to an initial position again. This is in particular used for a force-fit connection between the surgical connecting device 100 and the contact section 230 and/or 330. When the surgical connecting device is inserted, the movable parts 113 and 114 thus press against the boundary of the contact gap 232. Similarly, movable parts 124 and 123 (not shown) press against a boundary wall of the contact gap 332, wherein the contact part 125 is inserted into the contact gap 332. An abutment 116 and 126 is preferably situated at the rear end 112 and 222 of the contact parts 115 and 125, and forms an edge of the spacing section and is thus arranged between the attaching section and the spacing section. Once the surgical connecting device has been completely inserted into the contact sections 230 and 330, a front edge 234 and 334 of the contact section 230 and 330, respectively, abuts the abutment 116 and 126, respectively. In the embodiment shown in FIG. 3, this front edge is in each case in particular a front edge of the cutting plane gap 220 and 320.

The surgical connecting device 100 preferably has a U-shaped cross-section, as can be seen from FIG. 4. In the embodiment shown, the surgical connecting device has the shape of a three-dimensionally shaped letter U. The free ends of the three-dimensional letter U are inserted into the contact gaps 230 and 330. An intermediate space 140 is situated between the contact part 115 and the contact part 125. This intermediate space forms a space for parts 236 and 336 of the contact section 230 and 330, wherein the parts 236 and 336 opposite each other when the cutting blocks 200 and 300 are connected by the surgical connecting device.

The spacing section 130 can be divided into three sections 132, 134 and 136, which are preferably integrally connected to each other. The sections 132 and 136 are each components of the arms of the three-dimensional letter U. The section 134 forms the base of the three-dimensional letter U. A handle 136' can for example be attached to the base section 134. This handle can of course also be attached to the sections 132 and 136. However, the section 134 is preferred due to its superior accessibility. As also illustrated below, other devices—in particular a reference star (see FIG. 6) or a patella cutting device (see FIG. 7)—can also be attached to the spacing section 130 and in particular to its base part 134, which connects the arms of the three-dimensional letter U.

The movable parts 113, 114, 123 (not shown) and 124 each comprise an edge 113', 114', 123' (not shown) and 124' which tapers in the direction of the front end. The edge tapers in the direction of the front end and thus draws nearer to the exterior surface of the contact parts 115 and 125. Due to this taper, the movable parts 113, 114, 123 (not shown) and 124 are each pressed further and further in the direction of the surface of the contact parts 115 and 125 when the surgical connecting device 100 is inserted into the contact sections 230 and 330 of the cutting blocks 200 and 300, until the movable parts 113, 114, 123 (not shown) and 124 are aligned with the surface of the contact parts 115 and 125. Since they can be elastically moved, the movable parts press against a wall of the cutting gap when connected to the cutting blocks 200, 300, and thus ensure a force-fit connection. The movable parts 113, 114, 123 (not shown) and 124 can in particular be punched out of a common planar section by a punching process, said section in each case comprising a contact part and the assigned movable parts. The movable parts are then bent out of the plane which the contact parts form, so as to later be able to ensure a force-fit connection.

Figure 5:
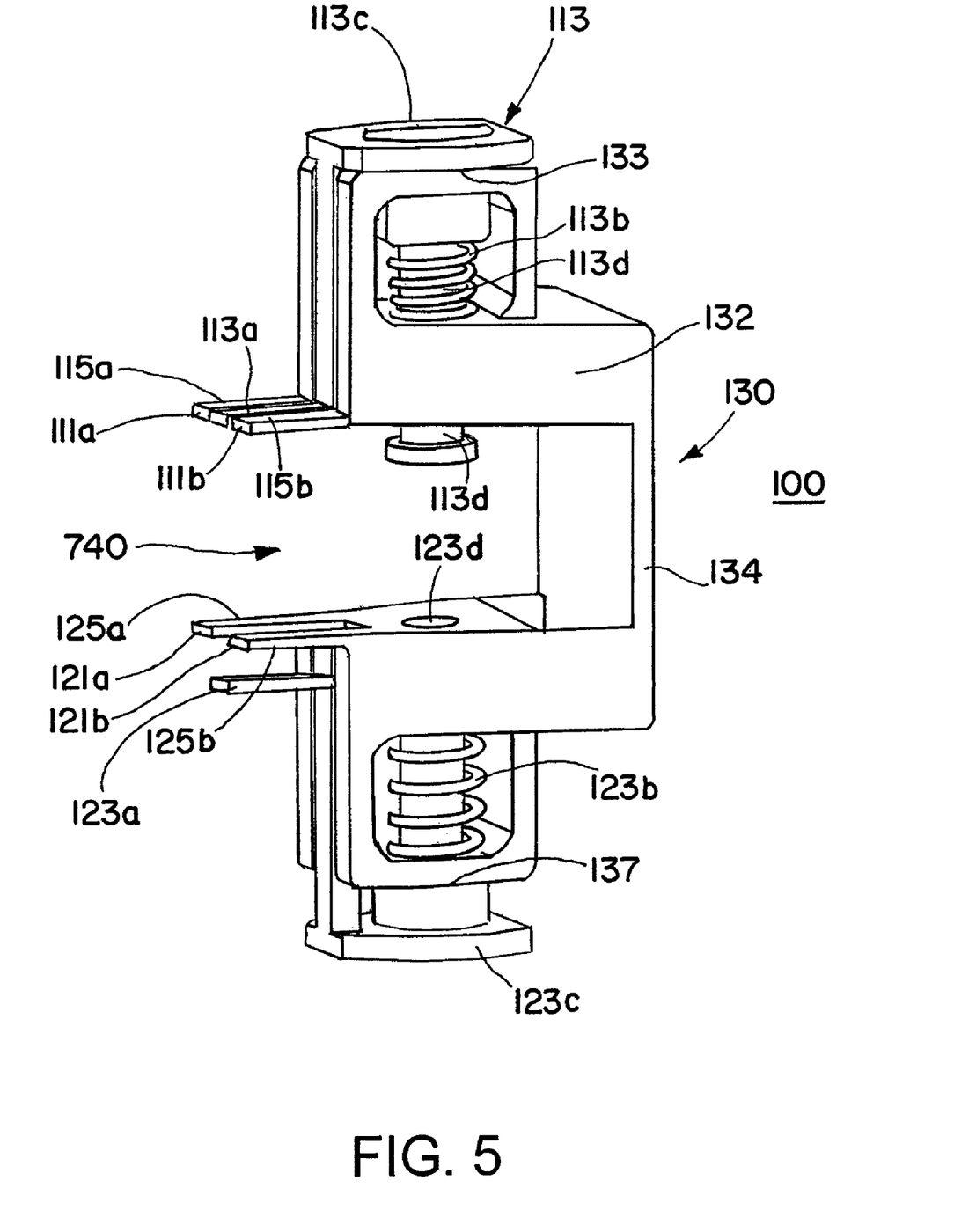
FIG. 5 shows another embodiment of the surgical connecting device in accordance with the invention.

FIG. 5 shows another embodiment of a surgical connecting device 100. Parts with an identical or similar function are indicated by the same reference signs. A spacing section 130 again has a U-shaped configuration. Contact parts 115a and 115b on one arm of the U-shaped connecting device, and 125a and 125b on another arm of the U-shaped connecting device, are again spatially fixed relative to the spacing section 130. Front ends 111a, 111b and 121a, 121b of the contact parts are formed so as to be inserted into the contact gaps. A movable part 113 comprises an insertion part 113a which can be moved into a plane in which the contact parts 115a and 115b lie. In the situation shown in FIG. 5, the insertion part 113a lies in the same plane as the contact parts 115a and 115b. The movable part 113 also comprises a spring 113b and an actuating button 113c comprising a cylinder 113d. The spring is supported with respect to the spacing section 130, more specifically with respect to the part 132 of the spacing section 130. If the button 113c is moved downwards, i.e. in the direction of the spacing section 130, then it is necessary to work against the force of the spring 113b which is supported on the part 132, wherein the cylinder 113d is pressed downwards until it assumes the position which can be seen in FIG. 5. When the push-button 113c abuts against an abutment 133 of the spacing section, the insertion section 113a is then also situated in the same plane as the contact parts 115a and 115b.

The lower part of FIG. 5 shows an actuating button 123c when it is not being pressed. The insertion section 123a is therefore also not in the same plane as the contact parts 125a and 125b. The spring 123b is relaxed. Therefore, as opposed to the cylinder 113d, the cylinder 123d does not protrude into the intermediate space surrounded by the U-shaped spacing section 130. Pressing the button 123c until the surface of the button 123c abuts against an abutment 137 of the spacing section 130 causes the insertion section 123a to lie in the same plane as the contact parts 125a and 125b.

Thus, once the buttons 113c and 123c have been pressed up to the abutments, the surgical connecting device can be inserted into the contact gaps of two cutting blocks. When the buttons 113c and 123c are released after the surgical connecting device has been inserted, a force-fit connection is thus obtained. The two cutting blocks 200, 300 are thus connected and thus spatially fixed relative to each other. The latter is a prerequisite for being able to adjust the desired position of two cutting blocks 200, 300 using one adjusting mechanism 400.

Figure 6:
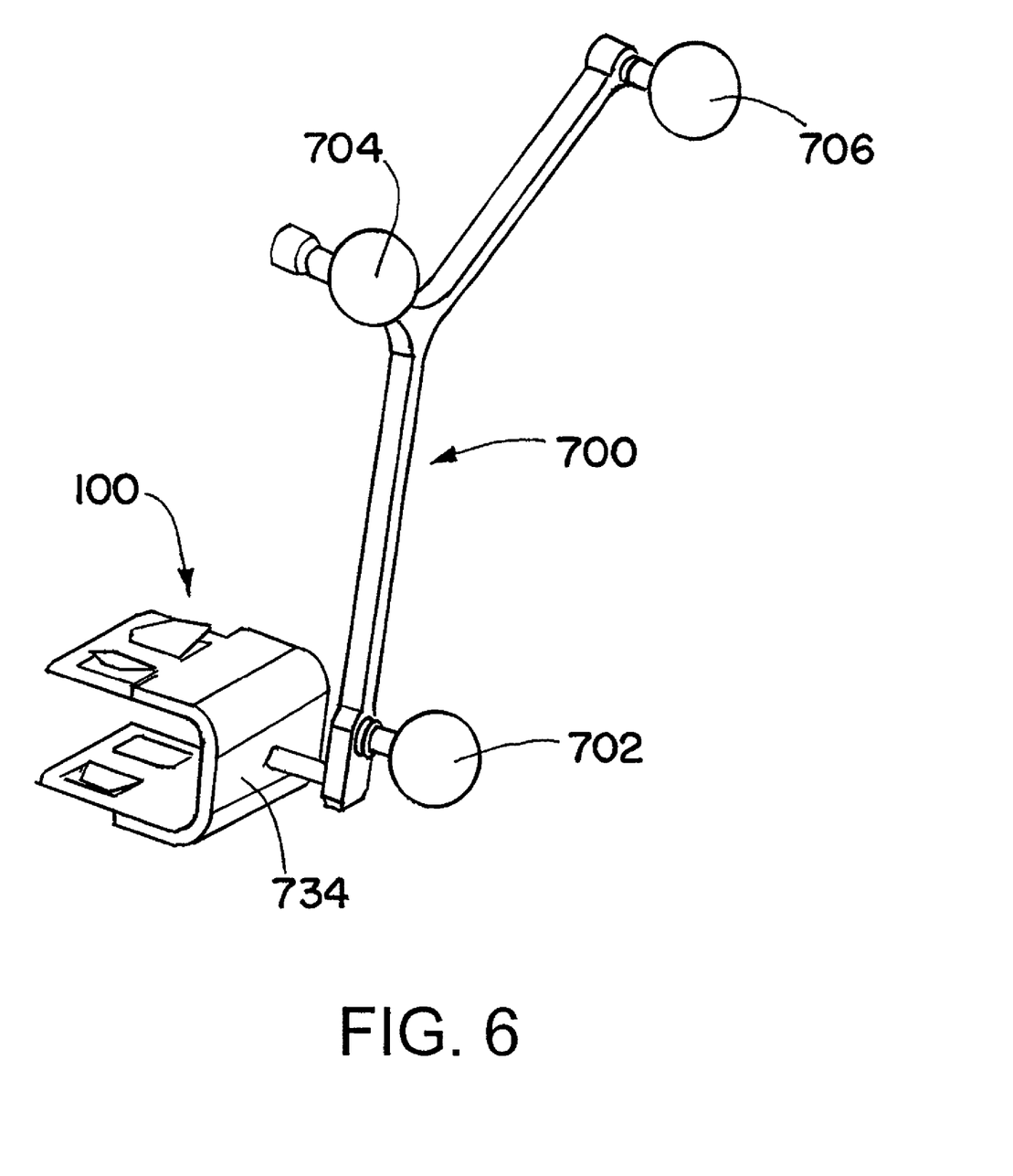
FIG. 6 shows a surgical connecting device in accordance with the invention, comprising a marker device.

FIG. 6 shows a surgical connecting device 100 comprising a reference star 700 attached to it which comprises marker elements 702, 704 and 706. The reference star 700 is attached to the base part 134 of the U-shaped surgical connecting device 100. With the aid of the reference star 700, it is possible to enable the surgeon to connect the surgical connecting device 100 to the contact sections 230, 330 of the cutting blocks 200, 300, even when visibility is poor. The reference star 700 can also be used in addition to this purpose (or exclusively) as a navigation aid for positioning the second cutting block 200, since a spatially fixed connection between the cutting block (in particular, the second cutting block 200) and the reference star 700 is given.

Figure 7:
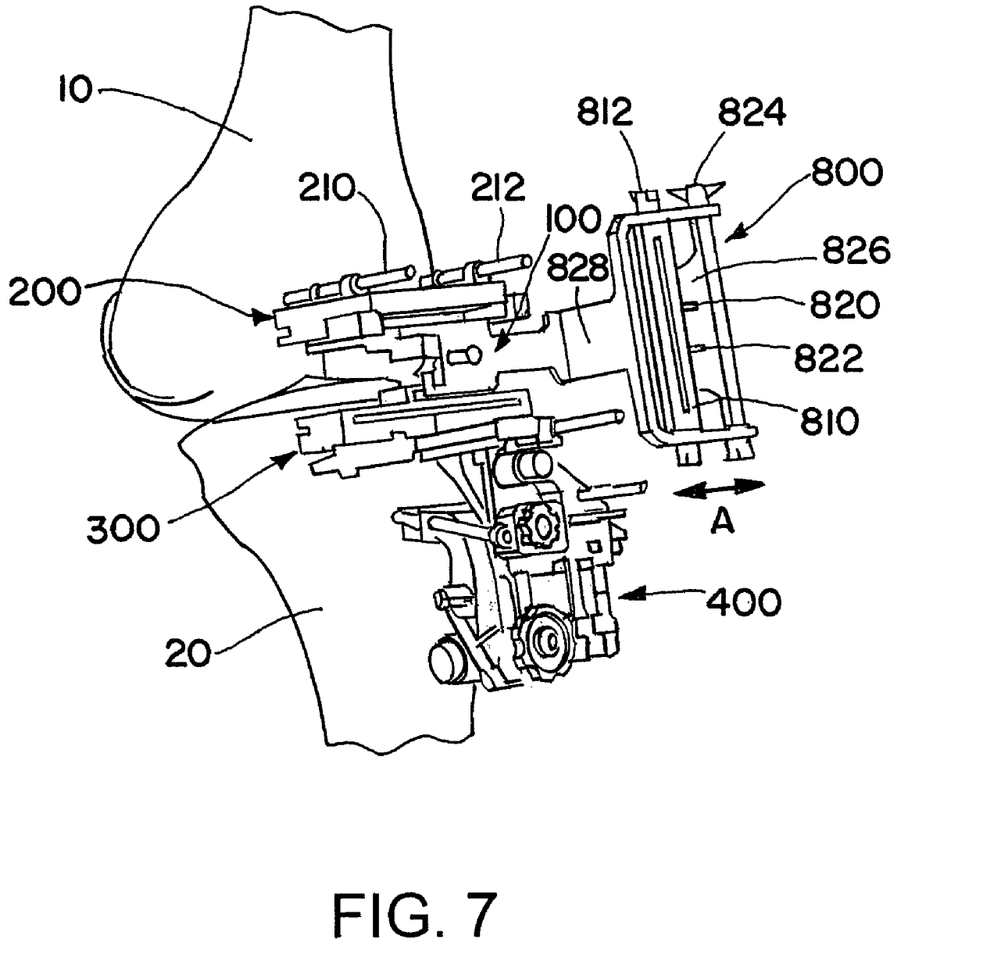
FIG. 7 shows a surgical system in accordance with the invention, comprising a patella cutting device in accordance with a first embodiment.

FIG. 7 shows the situation when the femoral cutting block 200 is fixed. The cutting block 300 is likewise fixed using pins. FIG. 7 relates to a second, alternative approach to the approach already described above. Accordingly, the position of the tibial cutting block 300 is adjusted first, with the aid of the adjusting mechanism 400. Then, the tibial cutting block 300 is fixed. The position of the femoral cutting block 200 relative to the femur is then adjusted by shifting the tibia and the femur, and the femoral cutting block 200 is then fixed. While the femoral cutting block is being fixed, it is in particular connected, spatially fixed, to the tibial cutting block 300 via the connecting device 100. In the alternative approach in accordance with FIG. 7, the adjusting mechanism 400 is accordingly only used to adjust the position of the tibial cutting block 300. The distance between the tibial cutting block 300 and the femoral cutting block 200 is determined by selecting a suitable connecting device or by adjusting the distance between the cutting blocks by means of the adjusting mechanism described above. The femoral cutting block 200 can then be positioned relative to the femur by shifting the femur and/or tibia. Adjusting the position of the femoral cutting block 200 relative to the femur by moving the tibia 20 and the femur 10 can also be used in the first approach already described above, in particular in order to make a rough adjustment. A fine adjustment can then be made in the first approach by means of the adjusting mechanism.

The adjusting mechanism 400 is also fastened to the tibia 20. A patella cutting device 800 is connected to the connecting device 100. In the scenario shown, the patella cutting device 800 is integrally connected to the surgical connecting device 100. The patella cutting device 800 comprises an adjustable cutting slit part 810 and two dorsal processes 820, 822 for fixing the patella. The cutting slit 810 can be adjusted by a screw 812 in the directions indicated by A. The distance from a rear abutment surface 826 can likewise be adjusted relative to the front abutment surface 828 by a screw 824. The front abutment surface 828 is connected, spatially fixed, to the connecting device 100. The patella can be clamped between the front abutment surface 828 and the rear abutment surface 826 by adjusting the rear abutment surface 826.

Figure 8:
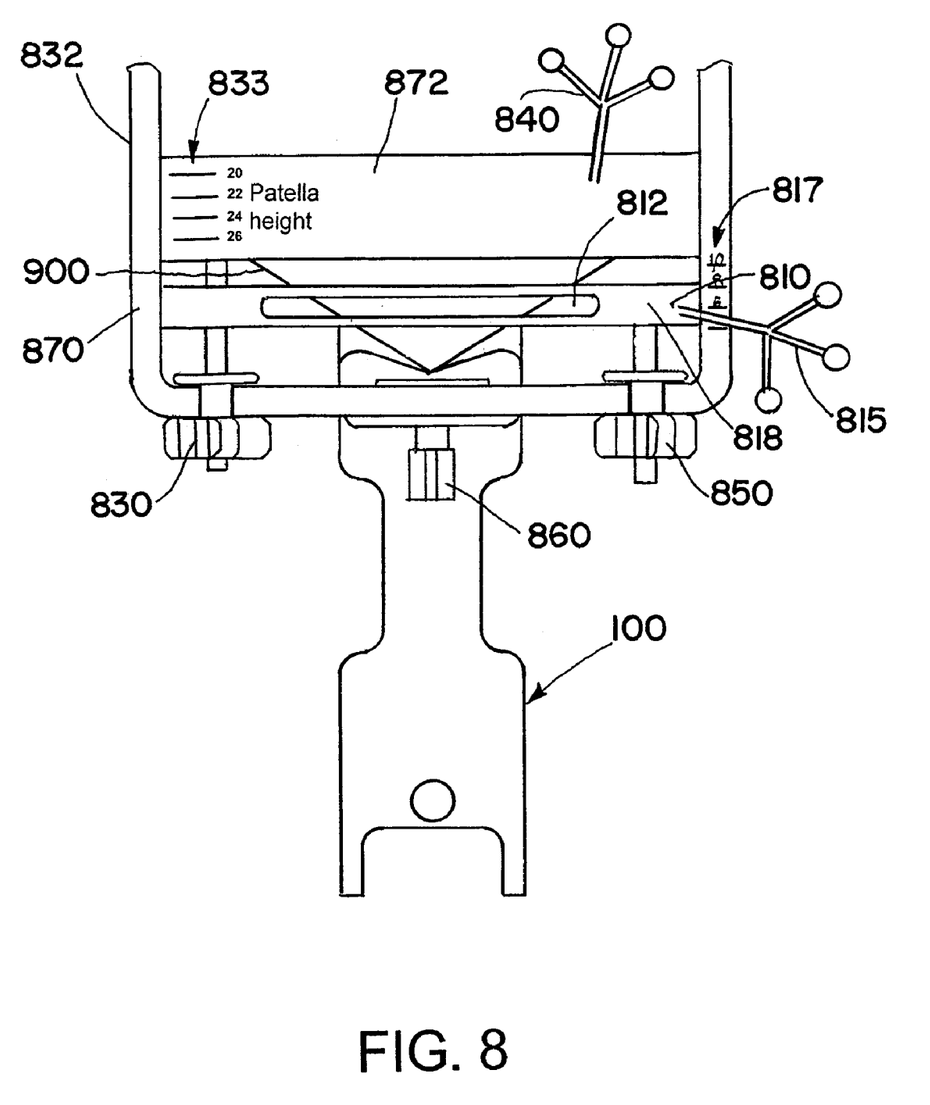
FIGS. 8 to 12 show a patella cutting device in accordance with a second embodiment, which is connected to the surgical connecting device by way of example.
Figure 9:
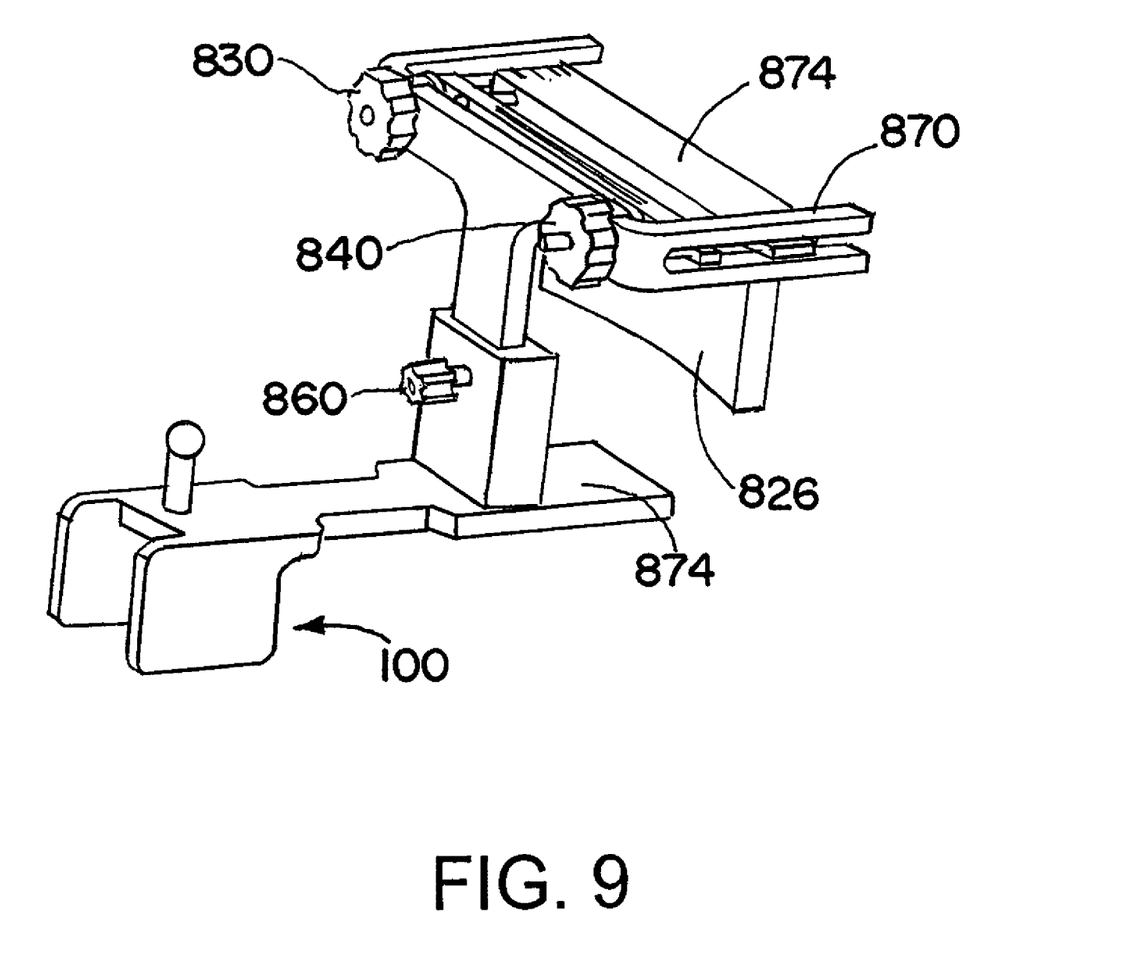

FIG. 8 shows an alternative embodiment of the patella cutting device 800. The distance between a rear abutment surface 826 and a front abutment surface 828 (see FIG. 9) can be adjusted by a screw 830. If the patella is clamped between the front and rear abutment surface, the patella height can be measured by means of a scale 833 and a scale mark 832. The rear abutment surface 826 is movable relative to the front abutment surface and relative to a frame 870. In accordance with one embodiment, a reference star 840 is attached to the rear abutment surface 826 or to a part which is spatially connected to it, for example the scale 833. The patella height can thus be automatically determined by a navigation system (which for example comprises the navigation device 600) by reading off the position of the reference star 840, without it being necessary to read off the scale 833 using the scale mark 832. Preferably, though not compulsorily, the patella cutting device comprises the connecting device 100 in accordance with the invention. The patella cutting device 800 can thus also be used without the connecting device 100 in accordance with the invention. In particular, the patella cutting device 800 without the connecting device 100 relates to another invention. This patella cutting device thus comprises an adjusting means 830 (for example, a turning knob 830) in order to adjust the distance between the front and rear abutment surface. It also preferably comprises an adjusting means (for example, an adjusting wheel 850) in order to adjust the cutting height. The adjusting wheel 850 is mechanically connected to a cutting slit part 810 which comprises a cutting slit 812 for inserting a blade for cutting the patella. A reference star 815 can likewise be attached, spatially fixed, to the cutting slit part 810. The adjusted cutting height can be determined by detecting the reference star 815 by means of the navigation device 600. Alternatively, the cutting height can be read off by reading off the scale 817 and the scale mark 818 (see FIG. 12).

Figure 10:
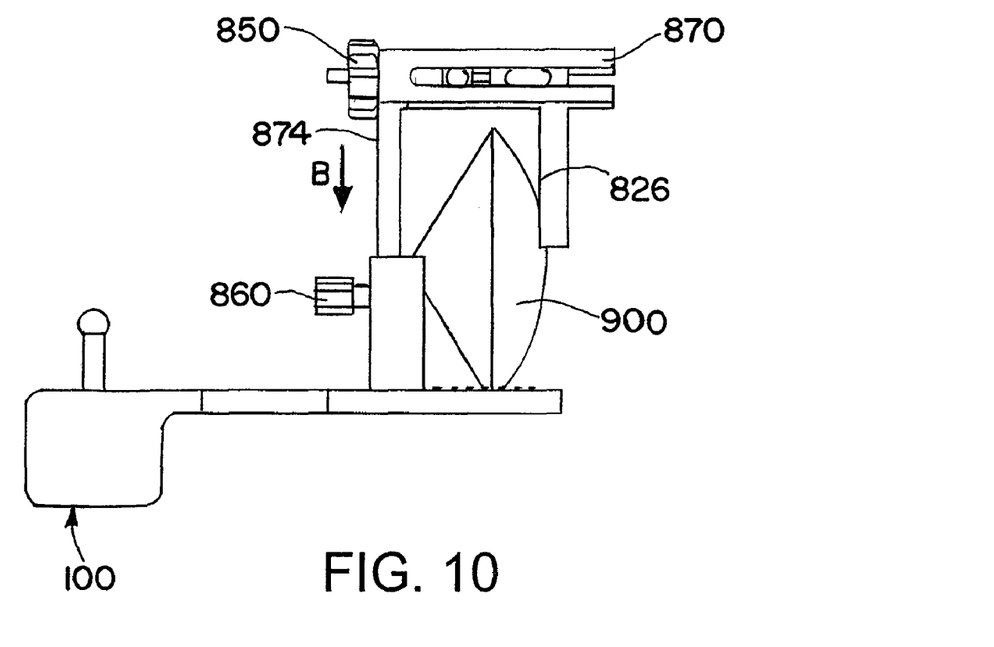
Figure 11:
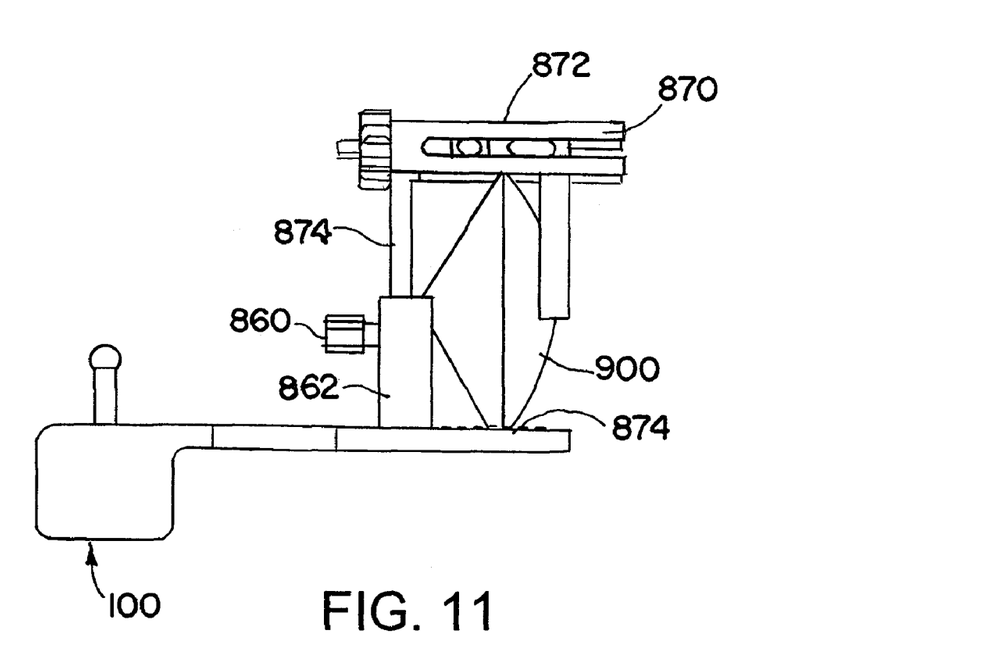
Figure 12:
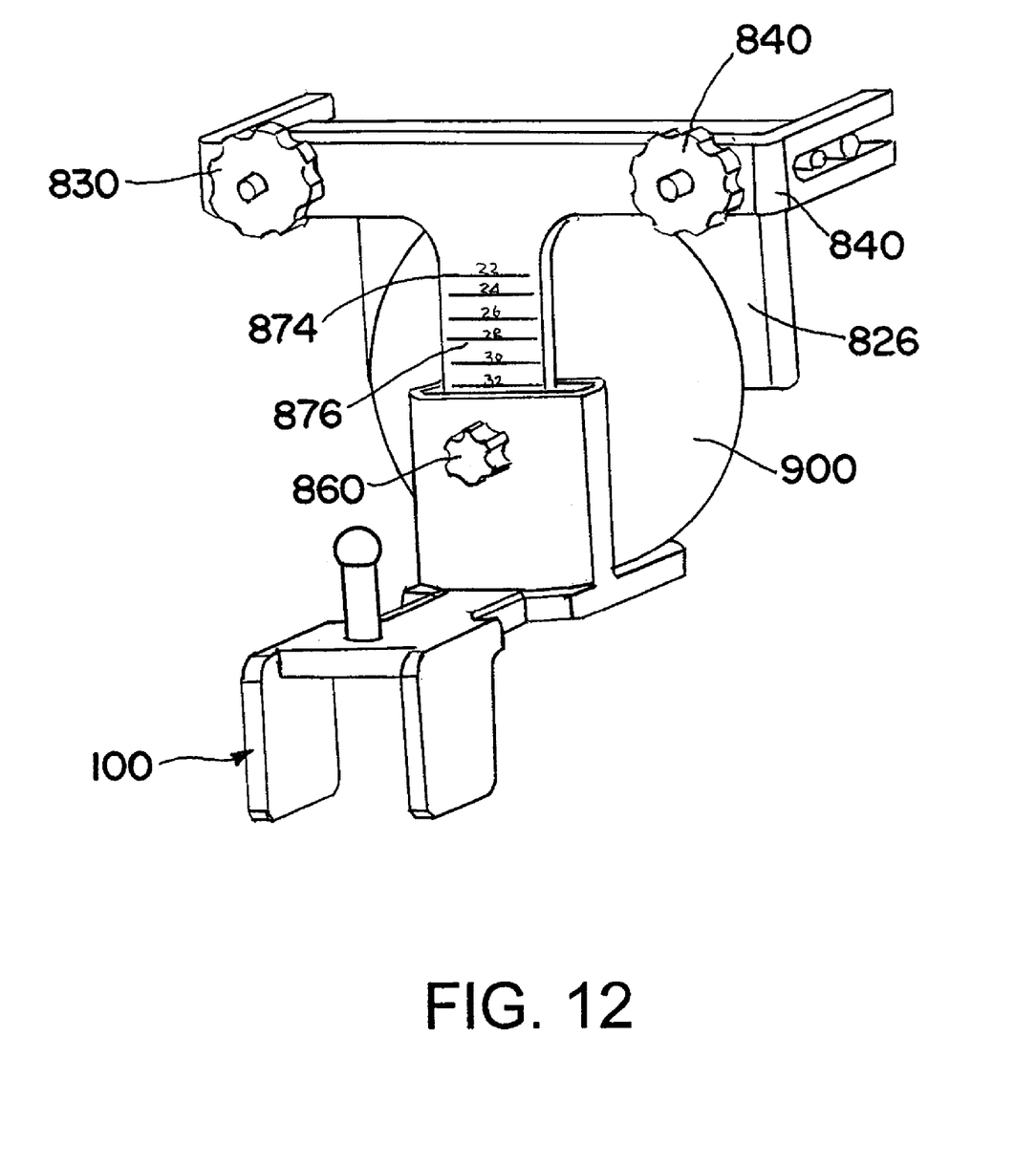

An adjusting part 860 allows patella abutment surfaces to be adapted to the diameter of the patella, as shown in FIGS. 10 and 11. An upper frame 870 can be lowered in the direction indicated by B. The lowered situation is shown in FIG. 11. In this situation, the frame 870 can then be fixed using the turning knob 860. FIG. 12 shows another view of the patella cutting device 800. The frame 870 is situated in its lowered position. This means that the full diameter of the patella 900 lies between a part 872 of the frame 870 and a bearing surface 874 which is preferably provided with nubs. The bearing surface 874 is preferably connected, spatially fixed, to a stand 862. The bar 874 of the frame 870 is in particular movable in the direction B (see FIG. 10). The bar 874 is fixed relative to the stand 862 by the adjusting wheel 860. In the embodiment shown in FIG. 11, the stand 862 is spatially fixed to the connecting device 100. As shown in FIG. 12, the patella diameter can be read off from a scale 876, when the part 872 of the frame 870 and the bearing surface 874 are each in contact with the boundary of the patella 900, in particular at opposite locations. The boundary of the patella 900 is typically oval or circular and runs along the exterior surface of the patella 900, where it has the largest circumference.

Computer program elements of the invention may be embodied in hardware and/or software (including firmware, resident software, micro-code, etc.). The computer program elements of the invention may take the form of a computer program product which may be embodied by a computer-usable or computer-readable storage medium comprising computer-usable or computer-readable program instructions, "code" or a "computer program" embodied in said medium for use by or in connection with the instruction executing system. Within the context of this application, a computer-usable or computer-readable medium may be any medium which can contain, store, communicate, propagate or transport the program for use by or in connection with the instruction executing system, apparatus or device. The computer-usable or computer-readable medium may for example be, but is not limited to, an electronic, magnetic, optical, electro-magnetic, infrared or semiconductor system, apparatus, device or medium of propagation such as for example the Internet. The computer-usable or computer-readable medium could even for example be paper or another suitable medium on which the program is printed, since the program could be electronically captured, for example by optically scanning the paper or other suitable medium, and then compiled, interpreted or otherwise processed in a suitable manner. The computer program product and any software and/or hardware described here form the various means for performing the functions of the invention in the example embodiments.

Although the invention has been shown and described with respect to one or more particular preferred embodiments, it is clear that equivalent amendments or modifications will occur to the person skilled in the art when reading and interpreting the text and enclosed drawings of this specification. In particular with regard to the various functions performed by the elements (components, assemblies, devices, compositions, etc.) described above, the terms used to describe such elements (including any reference to a "means") are intended, unless expressly indicated otherwise, to correspond to any element which performs the specified function of the element described, i.e. which is functionally equivalent to it, even if it is not structurally equivalent to the disclosed structure which performs the function in the example embodiment or embodiments illustrated here. Moreover, while a particular feature of the invention may have been described above with respect to only one or some of the embodiments illustrated, such a feature may also be combined with one or more other features of the other embodiments, in any way such as may be desirable or advantageous for any given application of the invention.

What is claimed is:

1. A surgical system comprising:
   first and second cutting blocks that serve to make an incision on a first and second anatomical structure respectively;

a surgical connection device having a first attaching section attaching the surgical connecting device to the first cutting block by a releasable mechanical connection, a second attaching section attaching the surgical connecting device to the second cutting block by a releasable mechanical connection, and a spacing section which non-adjustably spaces the first attaching section from the second attaching section; and an adjusting mechanism removably connected to the first cutting block, the adjusting mechanism configured to adjust the position of the first and second cutting blocks relative to the first and second anatomical structures.

2. The surgical system according to claim 1, wherein the spacing section for achieving the spacing connects the first attaching section to the second attaching section outside an intermediate space between the first and second attaching sections.

3. The surgical system according to claim 1, wherein the attaching sections comprise a front end and a rear end, wherein the spacing section is connected to the respective rear end of the first and second attaching section, wherein the front end lies on the side of the respective attaching section opposite the rear end.

4. The surgical system according to claim 1, comprising a marker device.

5. The surgical system according to claim 1, comprising a handle arranged on the spacing section, and/or wherein the spacing section comprises an adjusting mechanism using which the distance between the first and second attaching section can be adjusted.

6. The surgical system according to claim 1, comprising a patella cutting device.

7. A navigation system comprising a navigation device and the surgical system according to claim 1.

8. The system according to claim 1, further comprising a marker device coupled to the second cutting block.

9. The system according to claim 1, further comprising a marker device coupled to the spacing section.

10. The system according to claim 1, wherein the surgical connection device is U-shaped.

11. A surgical system comprising:
first and second cutting blocks that serve to make an incision on a first and second anatomical structure respectively;
a surgical connection device having a first attaching section attaching the surgical connecting device to the first cutting block by a releasable mechanical connection, a second attaching section attaching the surgical connecting device to the second cutting block by a releasable mechanical connection, and a spacing section which spaces the first attaching section away from the second attaching section; and
an adjusting mechanism removably connected to the first cutting block, the adjusting mechanism configured to adjust the position of the first and second cutting blocks relative to the first and second anatomical structures;
wherein the attaching sections comprise movable parts and contact parts, wherein the movable parts are elastically movable relative to the contact parts.

12. The surgical system according to claim 11, wherein the movable parts are elastically movable transverse to a plane which connects a front end and rear end of the attaching sections.

13. The surgical system according to claim 11, wherein the contact parts are formed to be planar and/or lie in one plane.

14. The surgical system according to claim 11, wherein the movable parts are chamfered in the direction of a front end of the attaching sections.

15. A surgical system comprising:
first and second cutting blocks that serve to make an incision on a first and second anatomical structure respectively;
a surgical connection device having a first attaching section attaching the surgical connecting device to the first cutting block by a releasable mechanical connection, a second attaching section attaching the surgical connecting device to the second cutting block by a releasable mechanical connection, and a spacing section which spaces the first attaching section away from the second attaching section; and
an adjusting mechanism removably connected to the first cutting block, the adjusting mechanism configured to adjust the position of the first and second cutting blocks relative to the first and second anatomical structures;
wherein abutment sections are provided between the spacing section and each of the attaching sections and serve as abutments when the attaching sections are inserted into cutting slits of the cutting blocks.

16. A method of attaching first and second cutting blocks to a first and second body structure which are connected via a joint, in a state in which an adjusting mechanism is fastened to the first body structure and connected to the first cutting block, and in which a connecting device having a first attaching section attaching the connecting device to the first cutting block by a releasable mechanical connection, a second attaching section attaching the connecting device to the second cutting block by a releasable mechanical connection, and a spacing section which spaces the first attaching section away from the second attaching section, the method comprising:
adjusting a position of the second cutting block relative to the first body part by means of the adjusting mechanism;
fixing the second cutting block to the second body structure;
removing the connecting device, such that the first cutting block which is connected to the adjusting mechanism is movable relative to the second cutting block;
adjusting the position of the first cutting block relative to the first body structure by means of the adjusting mechanism; and
fixing the first cutting block to the first body structure.

17. The method according to claim 16, wherein the position of the first and second cutting block is adjusted with the aid of detecting at least one marker device which is connected, spatially fixed, to the first cutting block at least at the time of adjusting the position of the first cutting block and is connected, spatially fixed, to the second cutting block at least at the time of adjusting the position of the second cutting block.

* * * * *